(12) United States Patent
Havard et al.

(10) Patent No.: US 7,319,522 B2
(45) Date of Patent: Jan. 15, 2008

(54) SYSTEMS AND METHODS FOR IN SITU SPECTROSCOPIC MEASUREMENTS

(75) Inventors: John M. Havard, Seattle, WA (US); Paul C. Williams, Livermore, CA (US)

(73) Assignee: Finesse Solutions LLC., Santa Clara, CA (US)

( * ) Notice: Subject to any disclaimer, the term of this patent is extended or adjusted under 35 U.S.C. 154(b) by 386 days.

(21) Appl. No.: 11/139,720

(22) Filed: May 27, 2005

(65) Prior Publication Data

US 2005/0264817 A1 Dec. 1, 2005

Related U.S. Application Data

(60) Provisional application No. 60/575,119, filed on May 27, 2004.

(51) Int. Cl.
*G01N 21/00* (2006.01)

(52) U.S. Cl. ...... 356/436; 356/432

(58) Field of Classification Search ...... 73/863–865, 73/84; 356/216–236, 432–448
See application file for complete search history.

(56) References Cited

U.S. PATENT DOCUMENTS

| | | | | |
|---|---|---|---|---|
| 3,609,047 A | * | 9/1971 | Marlow | 356/434 |
| 4,200,896 A | * | 4/1980 | Baumann | 345/55 |
| 4,666,672 A | * | 5/1987 | Miller et al. | 422/82.07 |
| 4,954,318 A | * | 9/1990 | Yafuso et al. | 422/59 |
| 5,005,005 A | * | 4/1991 | Brossia et al. | 340/604 |
| 5,313,940 A | * | 5/1994 | Fuse et al. | 600/310 |
| 5,316,950 A | * | 5/1994 | Apitz et al. | 436/28 |
| 5,402,777 A | * | 4/1995 | Warring et al. | 604/307 |
| 5,625,617 A | * | 4/1997 | Hopkins et al. | 369/121 |
| 5,742,581 A | * | 4/1998 | Ja | 369/275.1 |
| 5,798,940 A | * | 8/1998 | Bratton et al. | 700/267 |
| 6,115,061 A | * | 9/2000 | Lieberman et al. | 348/85 |
| 6,147,754 A | * | 11/2000 | Theriault et al. | 356/318 |
| 6,253,097 B1 | * | 6/2001 | Aronow et al. | 600/310 |
| 6,265,945 B1 | * | 7/2001 | Delaney et al. | 331/3 |
| 6,320,472 B1 | * | 11/2001 | Vanier | 331/94.1 |
| 6,567,166 B2 | * | 5/2003 | Ottens et al. | 356/343 |
| 6,615,064 B1 | * | 9/2003 | Aldrich | 600/316 |
| 6,771,374 B1 | * | 8/2004 | Rangarajan et al. | 356/445 |
| 6,819,950 B2 | * | 11/2004 | Mills | 600/322 |
| 6,950,260 B2 | * | 9/2005 | Coffey et al. | 360/59 |
| 7,061,593 B2 | * | 6/2006 | Braig et al. | 356/39 |
| 7,161,582 B2 | * | 1/2007 | Bathiche et al. | 345/156 |
| 2001/0020123 A1 | * | 9/2001 | Diab et al. | 600/323 |
| 2002/0101566 A1 | * | 8/2002 | Elsner et al. | 351/200 |
| 2003/0053244 A1 | * | 3/2003 | Lewis | 360/77.03 |

\* cited by examiner

*Primary Examiner*—Layla G. Lauchman
*Assistant Examiner*—Jarreas Underwood
(74) *Attorney, Agent, or Firm*—Herbert Burkard, Esq.

(57) ABSTRACT

A circularizated semiconductor laser diode (CSLD), such as for example a vertical cavity surface emitting laser (VCSEL) may be used for optical measurements. The CSLD may be used in a cell density probe to perform cell density determination and/or turbidity determination, such as in a biotech, fermentation, or other optical absorbance application. The cell density probe may comprise a probe tip section made from a polytetrafluoroethylene material, which provides sealability, ease of manufacture, durability, cleanability, optical semi-transparency at visible and near infrared wavelengths, and other advantages. The probe tip advantageously provides an optical gap that allows for in situ measurements of optical measurements including but not limited to absorbance, scattering, and fluorescence.

23 Claims, 6 Drawing Sheets

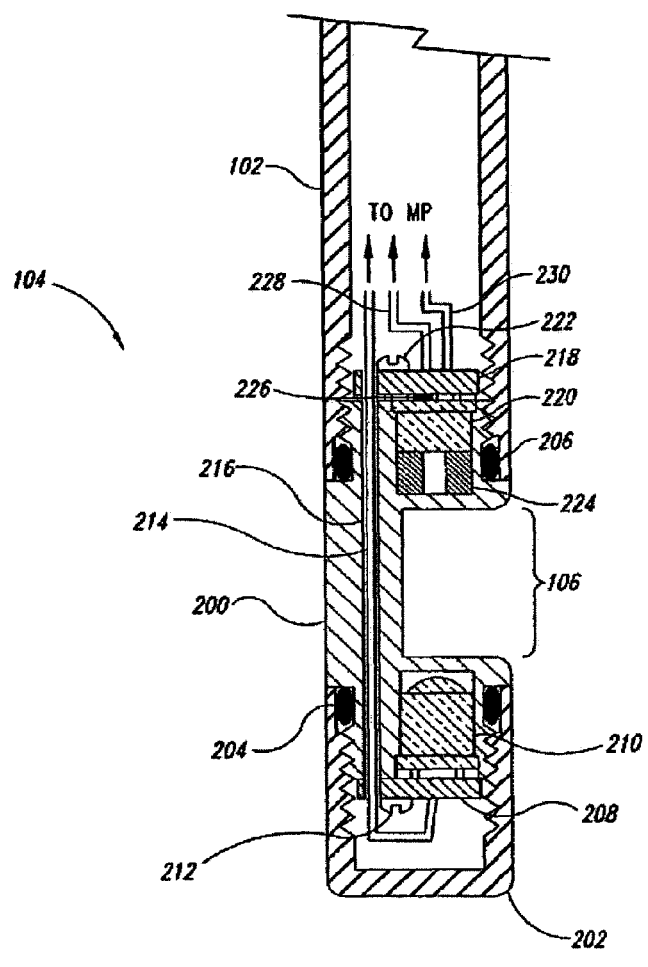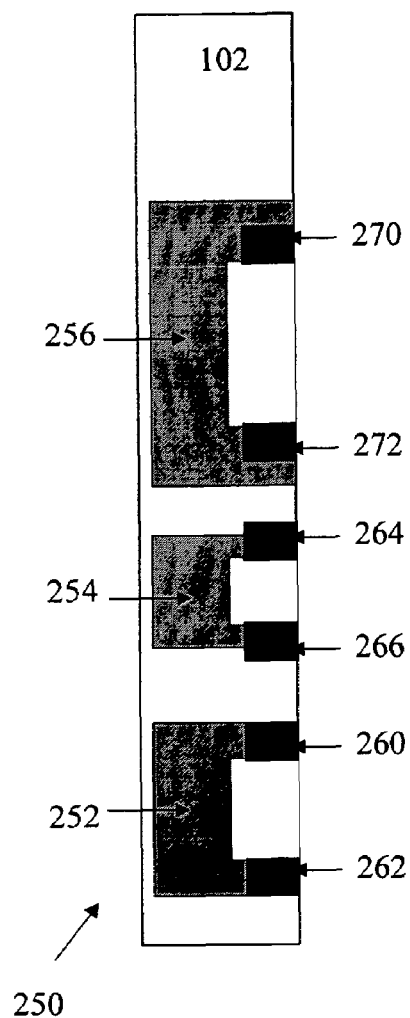
FIG.-2                    FIG.-3

US 7,319,522 B2

SYSTEMS AND METHODS FOR IN SITU SPECTROSCOPIC MEASUREMENTS

RELATED APPLICATIONS

This application claims the benefit of U.S. Provisional Patent Application Ser. No. 60/575,119, filed on 27 May 2004, the disclosure of which is hereby incorporated by reference in its entirety. This application is related to copending U.S. patent application Ser. No. 10/856,885:, entitled "Method and Apparatus for Verifying Proper Operation Of A Photometric Device, Such As a Cell Density Probe" filed on 27 May 2004, the disclosure of which is incorporated herein by reference in its entirety.

BACKGROUND OF THE INVENTION

1. Field of the Invention

The present disclosure is generally related to photometric devices, and particularly but not exclusively relates to photometric devices for performing light absorbance measurements.

2. Description of Related Art

There are several types of photometric devices used in a variety of different applications. In general, photometric devices include devices that are used to measure or otherwise determine one or more properties of light, such as intensity, color, wavelength, or other characteristics.

One type of photometric device is an optical absorbance sensor. One type of optical absorbance sensor is a cell density probe, which is used in biotechnology, chemical, brewery, wine, ethanol, fermentation, pharmaceutical, and other sectors of industry and/or research. With biotech applications, cell density probes are ordinarily used to monitor cell growth in a cell culture. In a typical implementation, live cells and some type of suitable growth agent (as well as possibly other additives) are placed in a vat or other vessel, with the growth agent, cells, and possibly other additives together forming a "broth" made up of liquid and suspended particulates (e.g., the cells). Conditions in the vat are then appropriately controlled to induce the cells to multiply and grow. The cells, once a sufficient amount have been grown, are harvested for various uses.

Cell density probes are used to monitor the cell growth in the vat at various times during the growing cycle, so as to ensure that the cells are growing at a proper rate and/or to verify whether a sufficient number of cells have been grown. Use of a cell density probe is an alternative to manual cell counting techniques, wherein cells in a sample from the vat are extracted and physically counted (and thus result in a high degree of error). In comparison, a density probe allows the number of cells to be automatically determined by correlation of light absorbance to cell density.

A typical cell density probe includes a tip that has an optical gap. The cell density probe is immersed into the vat, such that the optical gap and tip are completely covered by the broth. Light (at a specific wavelength or set of wavelengths) is transmitted from a first end of the optical gap to a second end of the optical gap. As the light passes through the optical gap, the cells present within the optical gap absorb and scatter a certain amount of the light. Therefore, the light received at the second end of the optical gap will have a lower intensity than the light transmitted from the first end of the optical gap, due to the absorbance and scattering of the light by the cells, which is typically expressed in terms of absorbance units (A.U.). The intensity of the received light decreases as the density of cells increase. Persons skilled in the art can correlate various intensities of the received light with growth rates and cell densities for the particular cell type that is involved. Accordingly, by monitoring the intensity of the received light over a period of time, the user of the cell density probe can determine if the growth rate is proceeding normally, if a sufficient number of cells have been grown, and/or whether a problem has occurred in the growing cycle. For example, if at a given wavelength the cell density probe provides a light intensity measurement that is higher than expected for that particular time in the growth cycle, then the higher intensity measurement at that wavelength may be indicative of contamination or other environmental condition that is impeding the capability of the cells to grow properly.

Existing photometric devices suffer from a number of disadvantages for use in biotech applications, including difficulty in manufacturing, bulkiness, unreliable or inefficient illumination components, complex structural parts, and other problems.

SUMMARY OF THE INVENTION

The present invention provides systems, methods, articles of manufacture, and apparatus that address problems in the prior art. The following brief summary of some of the claimed embodiments should not be construed as limiting on the scope of the claims.

In one embodiment, a method is provided for making photometric measurements. The method comprises the steps of emitting a beam of incident light from a circularized semiconductor laser diode (CSLD) in a photometric device such that the emitted light is incident on a sample and collecting and analyzing light transmitted through the sample.

In another embodiment, a method is provided for making photometric measurements, The method comprises the steps of emitting a beam of incident light from a circularized semiconductor laser diode (CSLD) in a photometric device such that the emitted light is incident on a sample; and collecting and analyzing fluorescent emissions occurring in the sample as a result of the incident light.

In another embodiment, a method is provided for making photometric measurements, The method comprises the steps of emitting a beam of incident light from a circularized semiconductor laser diode (CSLD) in a photometric device such that the emitted light is incident on a sample; and collecting and analyzing light scattered by the sample as a result of the incident light.

In another embodiment, an optical measurement system is provided. The system comprises means for emitting a beam of incident light from a circularized semiconductor laser diode (CSLD) in a photometric device such that the emitted light is incident on a sample volume, and means for collecting and analyzing light that is transmitted through, scattered by, or emitted within the sample volume.

In another embodiment, an article of manufacture is provided. The article of manufacture comprises a machine-readable medium for a photometric device, that has instructions stored thereon that are executable by a processor. The executable instructions cause the emission of light from a CSLD of the photometric device and the use of the light emitted from the CSLD in connection with optical measurements.

In another embodiment, an apparatus is provided for measuring optical absorbance. The apparatus comprises a tip section comprising a first light source and a first detector.

The first light source emits a first light beam at a first wavelength across a first optical gap towards the first detector such that the first detector receives the first light beam after the first light beam passes through the first optical gap and generates a first signal representative of the light received at the first detector. The apparatus further comprises a processor coupled to the first detector to determine an absorbance based on the first signal.

In a further embodiment, the apparatus may further comprise a second light source transmitting a second light beam parallel to the first beam and through the first optical gap onto a second photodetector such that the second light source emits light at a different wavelength than the first light source.

In an alternative embodiment, the apparatus may further comprise a second light source and a second detector. The second light source emits a second light beam at a second wavelength across a second optical gap towards the second detector, such that the second detector receives the second light beam after the second light beam passes through the second optical gap and generates a second signal representative of the light received at the second detector. The second signal is also coupled to the processor.

BRIEF DESCRIPTION OF THE DRAWINGS

Various illustrative aspects and advantages of the present invention will become apparent upon reading the detailed description of the invention and the appended claims provided below, and upon reference to the drawings, in which:

FIG. 2 is a side cross-sectional view of the probe tip section of a optical probe adapted for use in optical absorbance measurements according to one embodiment of the present invention.

FIG. 3 is a side cross-sectional view of an probe tip section of a optical probe adapted for use in with multiple path lengths according to one embodiment of the present invention.

FIG. 4a shows a cross-sectional side view for a probe used for low cell density measurements, while FIG. 4b shows side and top views, respectively, of a probe tip section used for high cell density measurements.

DETAILED DESCRIPTION OF EXEMPLARY EMBODIMENTS

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. The headings provided herein are for convenience only and do not interpret the scope or meaning of the claimed invention.

As an overview, a photometric device is provided for performing optical absorbance measurements. One non-limiting example of the photometric device is a cell density probe (CDP) that can be used to measure or approximate cell density based on the cell's light absorbency. An embodiment of the photometric device is provided with a vertical cavity surface emitting laser (VCSEL) as a light source, which has certain advantages over other types of light sources. One embodiment of the photometric device includes a sensor tip made from a molded polytetrafluoroethylene material, such as Teflon@, which has certain desirable advantages. The operation and structure of various embodiments of the photometric device will be apparent from reading this detailed description.

According to one embodiment, the VCSEL can be used for any suitable optical absorbance measurement application. According to another embodiment, the VCSEL is used in connection with on-line absorption measurements of cell density and/or turbidity, such as used in a CDP.

Overview of CDP Hardware Embodiments

Figure 1:
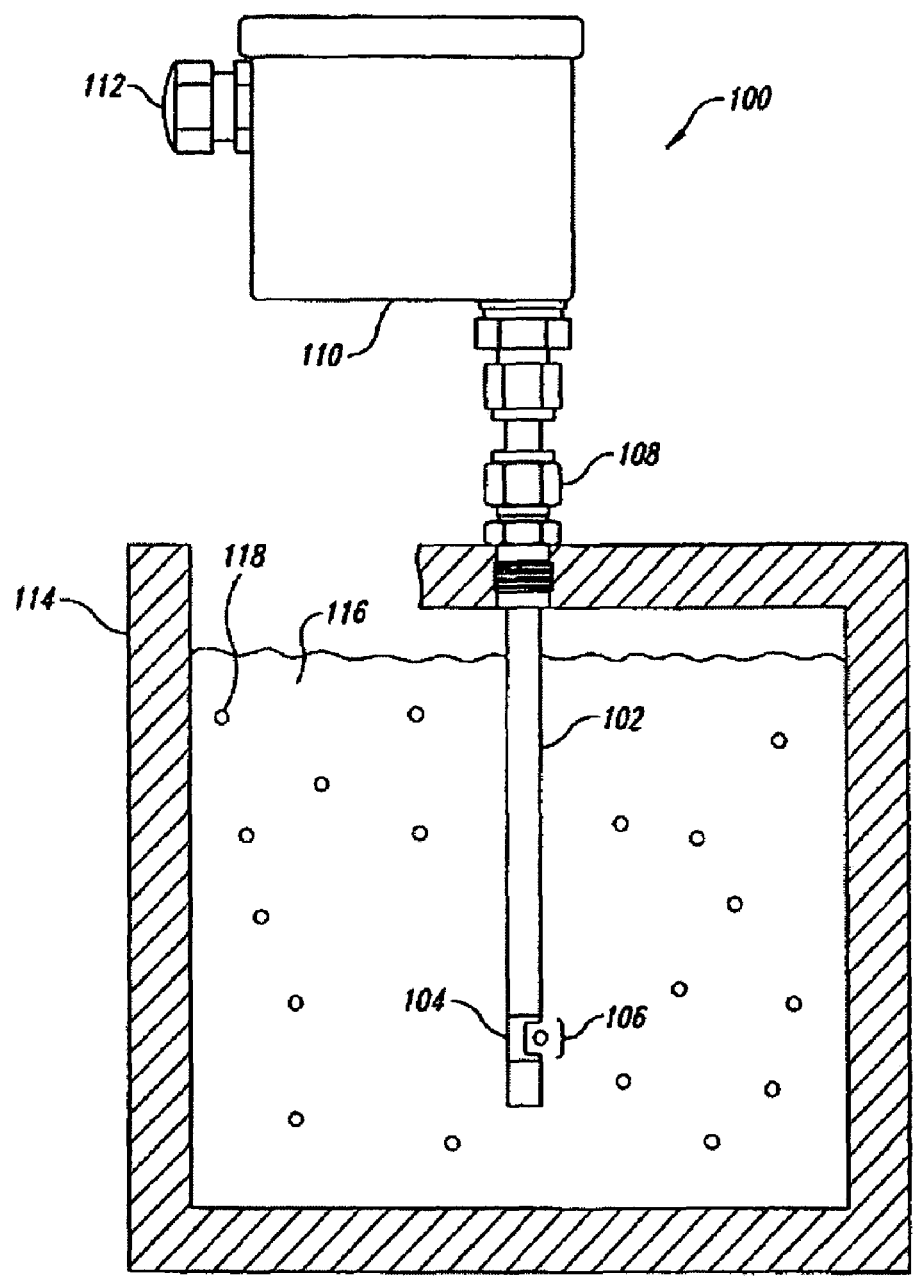
FIG. 1 is a side view of an embodiment of a cell density probe while in operation.

One embodiment of the CDP provides a probe for making a measurement of or approximating cell density by measuring optical absorbance. The wavelength of light used may range from the UV (approximately 200 nm) to the infrared (approximately 2000 nm). Advantageously, near-infrared radiation with a wavelength in the range of approximately 700 to 1000 nm may be used. In one embodiment, a wavelength of approximately 800 nm or alternatively of approximately 850 nm is used. FIG. 1 shows an example of a probe according to one embodiment of the present invention. Near infrared light is shown through a fluid medium across a precise gap 106, and a photodiode is used to detect the amount of light that is received. The unit 100 of FIG. 1 generally comprises two parts: a detachable probe 104 and an electronics housing 110.

Referring to FIG. 1, the probe 104 comprises the optical gap 106, with a light source and reference photodiode at one end and the main measurement photodiode at the other end. The probe may be used to make in situ optical measurements, for example of cell or particle density in a vat 114 holding a liquid medium 116 that contains suspended cells 118 or other microorganisms, particles, or the like. In other embodiments, a probe according to the present invention may be used for measuring optical absorbance in a liquid or gaseous medium where the absorbance is due to chemical, biological, or other materials present in the medium. As discussed in greater detail below, the probe is also adaptable for use in optical scattering or fluorescence measurements. While the many of the embodiments described herein make reference to optical absorbance, it should be understood by one of ordinary skill in the art that the teachings of the present invention are equally applicable to other forms of spectroscopic measurements. The description of optical absorbance embodiments should not be construed to limit the scope of the claims.

In one embodiment, a fitting 108 may be used to couple an electronic housing 110 to a vat 114. The electronic housing 110 may comprise a set of circuit boards that may be based on the desired user configuration. The electronic housing may optionally also comprise a CDP Core Function Module (CFM) board. For a wired embodiment, such as for example a probe employing a Foundation Fieldbus interface, a circuit board may be mounted on the CFM to provide the interface, as well as to provide power, for example at approximately 6V, to the CFM. One possible circuit board for such a wired interface may be purchased from Fieldbus Inc. (FDIP board). For a wireless interface, such as for example a probe comprising a Bluetooth wireless interface, a wireless board is mounted on the CFM to provide a wireless browser-based interface to the instrument. The wireless board may be obtained from, for example, connect-Blue (Bluetooth Web Enabler (BWE)) See, e.g., FIG. 5, discussed in greater detail below. In addition, an analog IO (AIO) board may be mounted on the CFM to provide the 6V power to the CFM and/or to the optional BWE, as well as to provide an isolated 4-20 mA output.

FIG. 2 shows an embodiment of the probe tip section 104 in more detail. It should be readily appreciated by one of ordinary skill in the art that the depicted structure of the tip section 104 is merely for explanatory purposes.

The probe section 102 may have a hollow tubular shape, made for example out of metal, and is advantageously coupleable to the tip section 104. The tip section 104 of one embodiment comprises a sensor head 200 made from an optically semi-transparent material. In one example embodiment, the sensor head 200 comprises a molded polytetrafluoroethylene material, such as Teflon®. In other embodiments, the sensor head 200 may comprise one or more materials selected from sapphire, glass, plastic, some other optically transparent or semi-transparent material, or the like.

Teflon® is an advantageous material for the probe tip due to several factors. The material is non-stick and therefore has excellent cleanability characteristics. Additionally, Teflon® is durable and can withstand heat, pressure, and other environmental elements. The material may be placed in an autoclave. The material is also relatively simple to manufacture or mold in uni-body form and assemble into the CDP 100, and provides an excellent sanitary seal because the sensor head is monolithic, which reduces the overall perimeter that requires sealing. This is in contrast to sapphire windows that generally require significant pressure to be pressed into the surrounding metal, have a larger sealing perimeter, and can therefore leak. Teflon® is also optically semi-transparent for a wide range of light wavelengths used by the CDP 100, including near infrared wavelengths.

The sensor head 200 may include threaded portions that mate with the threaded end of the probe section 102 and with threads of a sensor cap 202 (which itself may be made from the same material as the probe section 102). The threaded couplings, plus O rings 204 and 206 (which may be made from an ethylene-propylene-diene-monomer material, for example) ensure that neither the medium 116 nor other foreign material enter the interior of the tip section 104.

The length of the optical gap 106 may vary depending on the particular application involved. For example, shorter optical gaps may be provided in situations where the particular cells 118 have higher absorbencies as compared to other types of cells, or different optical gap lengths may be provided for biotech applications versus brewery applications, for example. Detailed discussion for determining the proper optical gap length are not provided herein, since such details would be familiar to those of ordinary skill in the art having the benefit of this disclosure. The proper gap length may be selected based on the measurement wavelength and application. The gap material may also be selected based on the measurement wavelength (for example, Teflon is not very transparent in the UV at 300 nm while quartz has excellent transmission properties)

Adjacent to the sensor cap 202 on one end of the optical gap 106, the sensor head 200 may be shaped to accommodate a photodetector assembly, and to insulate the photodetector assembly from the medium 116. The photodetector assembly of one embodiment comprises a circuit board 208 having a photodetector 210 (such as a photodiode) mounted thereon. A screw 212 or other suitable attachment mechanism (such as glue) may be used to fixedly attach the circuit board to the sensor head 200.

The sensor head 200 is defined with a channel 214 that advantageously accommodates one or more electrical leads 216 coupled to the photodetector 210. These electrical leads 216 carry electrical signals representative of the intensity of light detected by the photodetector 210, after that light has traversed through the optical gap 106. The electrical leads 216 may be coupled to conditioning electronics. The electrical signals are optionally converted into digital values that are read by a controller, microprocessor, digital signal processor, or other processor that cooperates with software to determine or otherwise calculate cell density (or an approximation thereof) based on the values of the detected light intensity, and/or to verify proper operation of the CDP 100.

At the other end of the optical gap 106, the sensor head 200 is advantageously shaped to accommodate a light source assembly, and may also be shaped to insulate the light source assembly from the medium 116. The light source assembly of one embodiment comprises a circuit board 218 having a light source 220 mounted thereon.

The light source 220 may comprise a light emitting diode (LED), other type of laser, incandescent light bulb, infrared light bulb, lamp, or other type of light source. In general, one embodiment for the light source is a circularized, semiconductor laser diode (CSLD). The CSLD may be a Fabry-Perot laser diode having a circularization lens directly mounted on one of its facets (such as supplied by BlueSky Research) or a DFB laser diode having a circularizing lens inside its package (such as supplied by Sharp or Toshiba). The CSLD advantageously has a small divergence angle in its emitted radiation. In one embodiment, the light source 220 advantageously comprises a Vertical-Cavity Surface-Emitting Laser (VCSEL).

A screw 222 or other suitable attachment mechanism, such as for example glue, machined slots, grass frit, and the like, may be used to fixedly attach the circuit board to the sensor head 200. An aperture 224, which may for example be made from an acetal resin material, such as black Delrin®, may be provided to prevent light from the light source 206 from scattering and propagating to the photodetector 210 via the solid material of the sensor head 200, rather than through the optical gap 106.

A reference photodetector 226 may optionally be also mounted on the circuit board 218. The photodetector 226 operates to detect the intensity of the light emitted from the light source 220 prior to reduction of the light's intensity due to absorbance by cells 118 in the optical gap 106. The photodetector 226 measures light directly output from the light source 220 and/or can measures light scattered or reflected therefrom.

One or more electrical leads 228 couples the photodetector 226 to the conditioning electronics, thereby allowing detected intensity values from the photodetector 226 to be provided to the processor. One or more electrical leads 230 is coupled between the light source 220 and the electronics, thereby allowing the light source 220 to be turned ON or OFF, and to change (such as reduce or increase) the current signal supplied to the light source 220 during verification operations.

The embodiment shown in FIG. 2 is adapted for use in optical absorbance measurements. Other embodiments may be implemented for tip sections 104 that have different structures or components. For example, as shown in FIG. 3, to facilitate simultaneous measurements at multiple wavelengths, the probe may contain multiple tip structures either in series or in parallel. For an embodiment in which the tip structures are in parallel, the gap size may be the same for all wavelengths. For a serial tip structure, different gap sizes may be used for different wavelengths. The probe tip 250 of FIG. 3 includes a first optical gap 252 with a first optical pathlength $L_1$, a second optical gap 254 with a second optical pathlength $L_2$, and a third optical gap 256 with a third optical pathlength $L_3$. The first optical gap 252 is formed between a first light source 260 and a first detector 262. The second optical gap 254 is formed between a first light source 264 and a first detector 266. The third optical gap 256 is formed between a first light source 270 and a first detector 272.

Figure 4B:
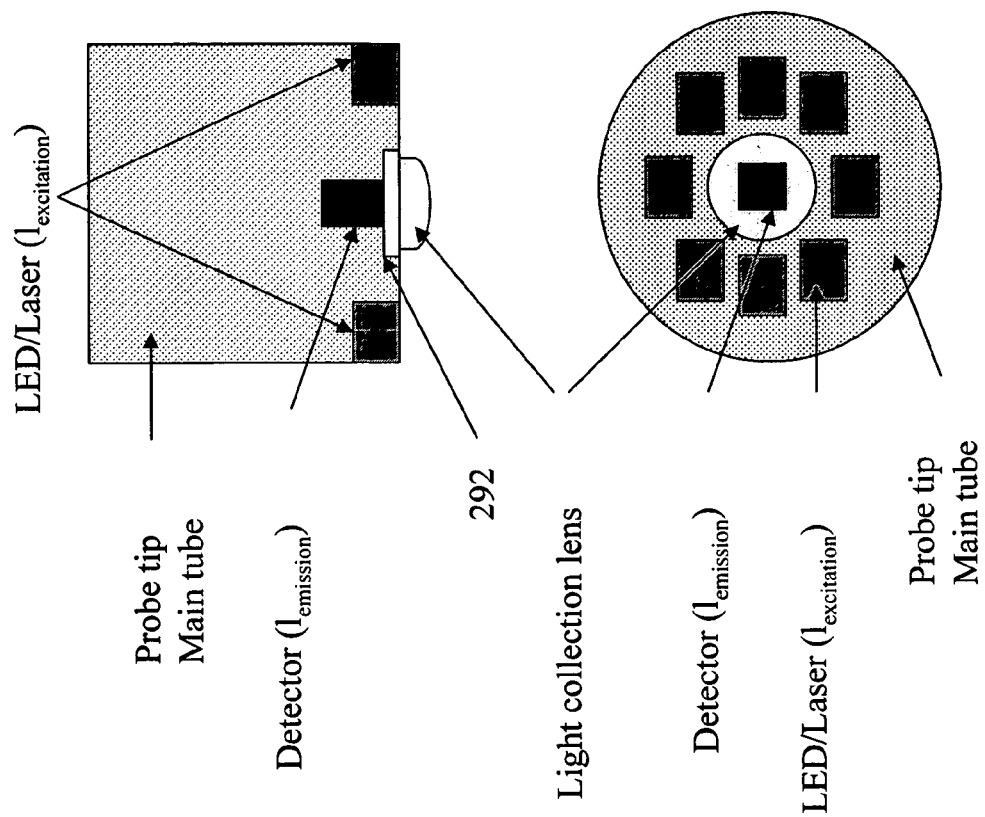
FIG. 4a and FIG. 4b show two different configurations for a probe tip section of an optical probe adapted for used in fluorescence and/or scattering measurements.
Figure 4A:
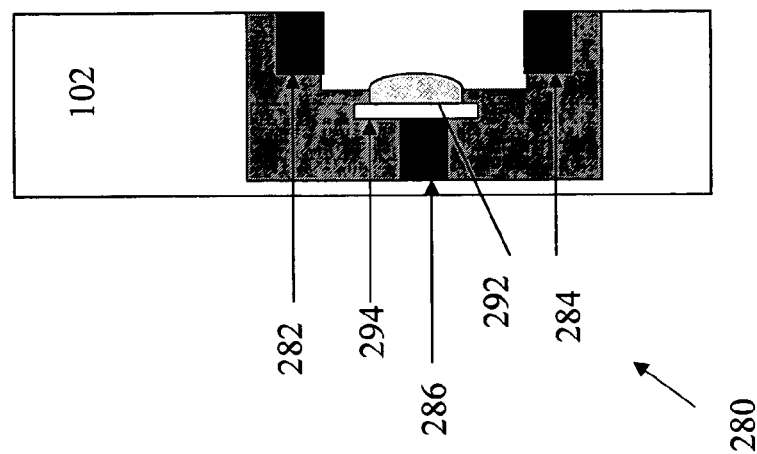

FIG. 4a and FIG. 4b show examples of a probe tip 280 for use in scattering or fluorescence measurements. As shown, in FIG. 4a and FIG. 4b, the probe tip 280 comprises a light source 282 providing excitation light at a wavelength $\lambda_{excitation}$ and two detectors: an on-axis (or excitation) light detector 284 and an off-axis (or emitted) light detector 286. The on-axis light detector 284 detects incident excitation light at $\lambda_{excitation}$ that passes through the optical gap 290, while the off-axis light detector 286 detects scattered light at $\lambda_{excitation}$ for a scattering measurement, or fluoresced light emitted at an emission wavelength $\lambda_{emission}$ for a fluorescence measurement. The off-axis light is optionally and advantageously collected and focused using a light collection lens 292 and filtered for the appropriate wavelength ($\lambda_{excitation}$ or $\lambda_{emission}$) by an optical filter 294.

Light Source and Detector Embodiments

The light source 220 may be a CSLD such as for example a VCSEL that emits near infrared light at a wavelength of 850 nm. An example VCSEL that can be used is the OPV210 available from Optek Technologies. The CSLD may be lensed or not lensed. Since CSLDs inherently have a narrow beam angle, it has a narrow beam divergence of approximately 12 degrees, even without a focusing lens. The laser package may also contain an integral silicon photodiode that may be used as an output power monitor. This photodiode may be used as the reference detector 226. This photodiode has a response bandwidth that includes the VCSEL emission wavelength, for example.

The use of a CSLD as a light source 220 has a number of advantages over a traditional LED approach. For example, the on-axis light output intensity of a CSLD is much higher, as much as 60 or 70 times higher, than an LED or lamp for a given current. This allows the light source 220 to be driven continuously, rather than pulsing an LED or lamp to extract a peak power, while maintaining sufficient light at the measurement detector 210. The higher optical power of a CLSD generally improves the signal to noise of CDP measurements and allows measurements of highly absorbing liquid media (where LED or lamp systems are photon-limited). The CSLD also has a high efficiency compared to a standard lamp, so that it lowers the power consumption of the CDP 100 enough to be loop-powered for Foundation Fieldbus applications.

Furthermore, the radiation emitted by a CSLD is coherent, rather than incoherent as for an LED or lamp, so that its spectral distribution is much narrower, and hence its transmission through the optical system is more consistent, even under varying experimental conditions. The spectral distribution of a CSLD may be approximately 25 times narrower than a LED and approximately 200 times narrower than a lamp. This means that the transmission signal through a tested medium will not substantially change unless there is a specific change in absorbance at the target wavelength. For lamp or LED based systems, the transmission measured is integrated over a wavelength range, so that transmission may not change even though the absorption at one specific wavelength may, in fact, change dramatically.

Additional advantages of using a CLSD as the light source may also be realized. The lesser divergence of CSLD light sources reduces light that reflects off the Teflon surfaces and reaches the measurement detector via a leakage path inside the Teflon head. In other words, coherent radiation is more easily spatially collimated over longer path lengths and can define a more consistent measurement volume in the sample. Additionally, the conditioning electronics become simpler, since the fast response time needed to accommodate lamp pulsing is difficult to achieve over a wide dynamic range. The reference diode 226 is built in to the CSLD, greatly simplifying assembly, and the output intensity and wavelength vary much less over temperature for the CSLD than for an LED.

A VCSEL is a particularly advantageous CSLD because by its geometry, it already produces a low divergence, circular beam. Moreover, the VCSEL has a high reflectivity output facet which minimizes its sensitivity to optical feedback from the optical cell, and the VCSEL has a very short laser cavity so that it is typically single mode, and hence produces a truly shot-noise-limited optical absorption system that is also stable in wavelength. Henceforth, we will describe one embodiment using a VCSEL, with the understanding that it is not limiting to the ideas described here.

In this embodiment, the main measurement detector 210 is a silicon photodiode. This part may be lensed with a narrow acceptance half-angle to minimize stray light pickup. It may have a peak response wavelength close to the VCSEL output wavelength. The reference and main photodiodes may have the same peak response wavelength and frequency response curve. If the VCSEL output wavelength varies as a function of temperature, the response of the two photodiodes should advantageously track each other.

A photodetector in the form of a photodiode has been described with regards to the photodetectors 210 and 226. The photodetectors 210 and 226 have also been described with respect to generating current signals that are representative of the light incident thereon. It is appreciated that other types of photodetectors (and their respective signals) may be implemented with other embodiments. For example, voltage signals, wireless signals, optical signals, or other signals may be used to represent one or more characteristics of light (such as intensity, wavelength, color, and the like) detected by a photodetector. The photodetectors 210 and 226 may be implemented as phototransistors, photoresistors, charge coupled devices (CCDs), or other photosensitive devices in other embodiments.

Core Function Module (CFM) Daughter Card Embodiments

Figure 5:
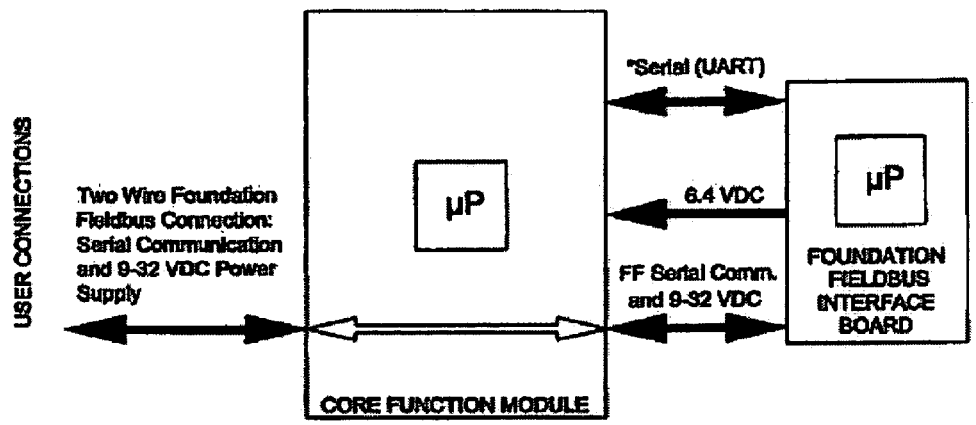
FIG. 5 is a block diagram of an example card configuration embodiment for the cell density probe of FIG. 1.
Figure 6:
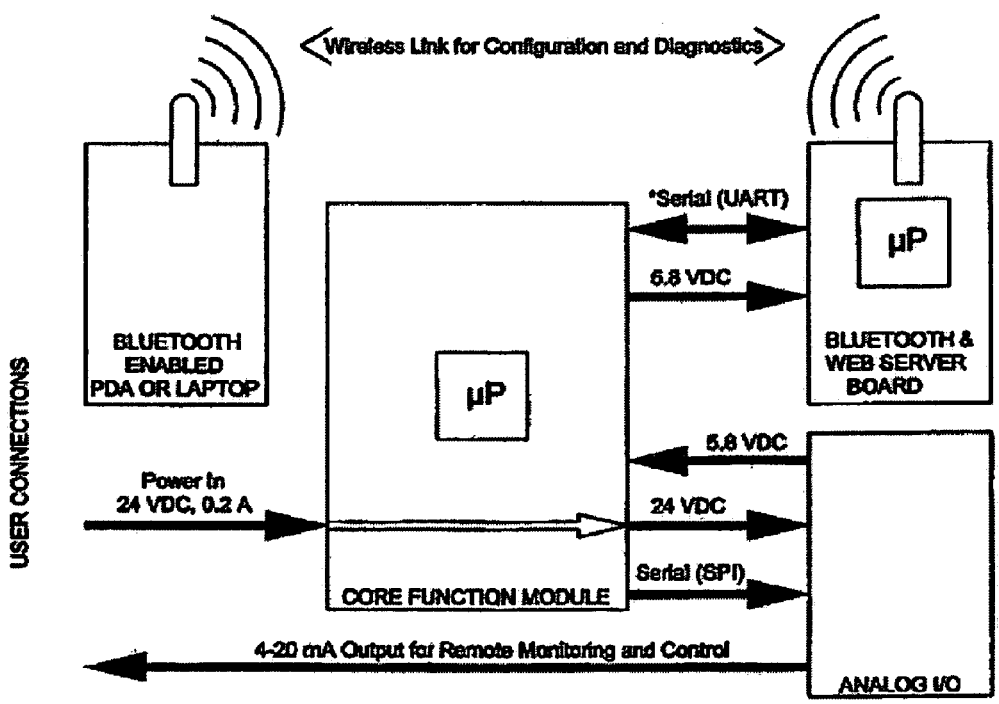
FIG. 6 is a block diagram of another example card configuration embodiment for the cell density probe of FIG. 1.

The CDP Core Function Module (CFM) board is the main board in the CDP electronics housing assembly. The cables from the light source 220 and detectors 226/210 in the probe tip 104 connect to this board, as shown for example in FIG. 2. Two additional possible daughter card configuration embodiments, one using a Bluetooth wireless interface in conjunction with an industry-standard 4 to 20 mA control output, and the other using a Foundation Fieldbus (FF) interface are shown in FIG. 5 and FIG. 6, respectively.

In one embodiment, a Bluetooth Web Enabler (BWE) card from connectBlue is mounted on the CFM board. The Bluetooth card contains an embedded web server and provides a wireless web browser interface for setup/configuration and measurement value display. The Bluetooth configuration option also includes installation of the Analog IO (AIO) card. The AIO card provides a user accessible industry standard isolated 4-20 mA current output. Other user connections on the CFM may comprise a DC power source, such as for example 24VDC, and ground.

In another embodiment, the FDIP Foundation Fieldbus card supplied by Fieldbus, Inc. is mounted on the CFM board. The FDIP card handles all the Fieldbus communications. In this configuration, the CDP is loop-powered, and both communication and power are provided to the instrument with the two FF wires. These FF wires are connected to the CFM board. The Fieldbus connections are routed to the FDIP board through the CFM, and the FDIP board is responsible for drawing the necessary power from the Fieldbus.

Light Source Driver Embodiments

In one embodiment of the present invention, the light source driver circuitry 312 provides a stable operating current to the light source 220. If the light source 220 is a CLSD or a VCSEL, it may be driven with a nominal current of 12 mA. This current may be increased or decreased for diagnostic purposes, adjusted to provide more or less light at different optical path lengths (OPLs), or controlled using the reference diode output in a feedback loop to regulate optical output power. The VCSEL current may be limited to 16 mA for up to 70° C. operation. A minimum current of approximately 6 mA may be used to ensure that the VCSEL operates above its turn-on threshold. In another embodiment, the VCSEL current may be kept at 12 mA under all operating conditions and with all OPLs, except for diagnostic purposes.

The circuit may operate by setting a precise voltage at the input to an op-amp and using the op-amp to control the gate voltage of a P-channel MOSFET such that this set voltage is maintained across a precision resistance. This circuit maintains a steady light source current that is independent (within the design range) of supply voltage and the voltage drop across the lamp. In addition, a measurement of the actual lamp current may be achieved using a sense resistor and current monitoring IC or circuit. For example, in one embodiment, a current monitor IC may provide a voltage to the A-to-D converter that is proportional to the lamp current. The resulting A-to-D converter reading may be compared in software to the known set voltage. It then follows that the current sense reading may be used as verification that the light source is connected and operating properly and as a test of the lamp driver circuitry.

As a further note, the current sense reading through the ADC may also contain the current through the reference photodiode, providing the reference photodiode is integrated into the CLSD or VCSEL package. This is normally much lower than the VCSEL drive current, contributing only a minor error to the measured lamp current. However, if this current sense reading is higher than the expected value, it may indicate a high leakage current through the reference photodiode 226.

A solid-state switch may be used in front of the op-amp to switch the lamp on and off. This feature could allow for pulsed lamp operation in an example embodiment. In addition, it may be used to switch between two current settings, rather than just off and on.

Analog Measurement Circuitry Embodiments

The CDP may be used to measure the absorbance of a solution, suspension, colloidal mixture, or other fluid system. The fundamental unit for an absorbance measurement is Absorbance Units, or A.U. Absorbance is defined as the logarithm (base 10) of the ratio of the intensity of the light transmitted through a reference medium ($I_0$) to the intensity of the light transmitted through the medium of interest ($I_T$):

$$\text{Absorbance(A.U.)} = \log \frac{I_0}{I_T} = -\log \frac{I_T}{I_0} = -\log\left(\frac{\% \text{ transmitted light}}{100}\right),$$

wherein the reference is defined as 100% transmitted light.

If a silicon photodiode is used as a detector, it typically outputs a current that is proportional to the intensity of the light incident on it over a very wide current range—approximately 1 mA to 1 nA. For example, assuming that the light through the reference medium generated a photodiode current of 1 mA, this would be considered the "zero" point or reference current. If the light transmitted through the medium of interest generated this same current of 1 mA, the Absorbance would be 0 A.U. For a measured photodiode current of 10 uA, Absorbance would be 1 A.U. Measured currents of 10 uA, 1 uA, 100 nA, 10 nA, and 1 nA would correspond to 2, 3, 4, 5 and 6 A.U. readings respectively. This, of course, assumes that the light source and the optical path remain constant after the reference current is measured.

For measurements of up to a 6 decade current range, direct linear A-to-D conversion of current to bits with reasonable accuracy would typically use either an A-to-D converter (ADC) with a high number of bits, or a variable gain amplifier in front of the ADC with an extremely wide gain range. In addition, logarithmic calculations would then be provided in software. In an alternative embodiment of the present invention, an analog logarithmic amplifier (log amp) may be employed as a front end. The log amp receives a current input and provides a voltage output proportional to the log ratio of the current input relative to a reference current. The log amp output is proportional to the logarithm of the light intensity at the photodiode. Once this signal has been converted to a digital reading and read by the microprocessor, absorbance can be calculated in software using the absorbance equation defined previously. In this manner, the front end log amp reduces the gain range that must be processed by the ADC. The logarithmic calculations are provided in hardware instead of software.

Figure 7:
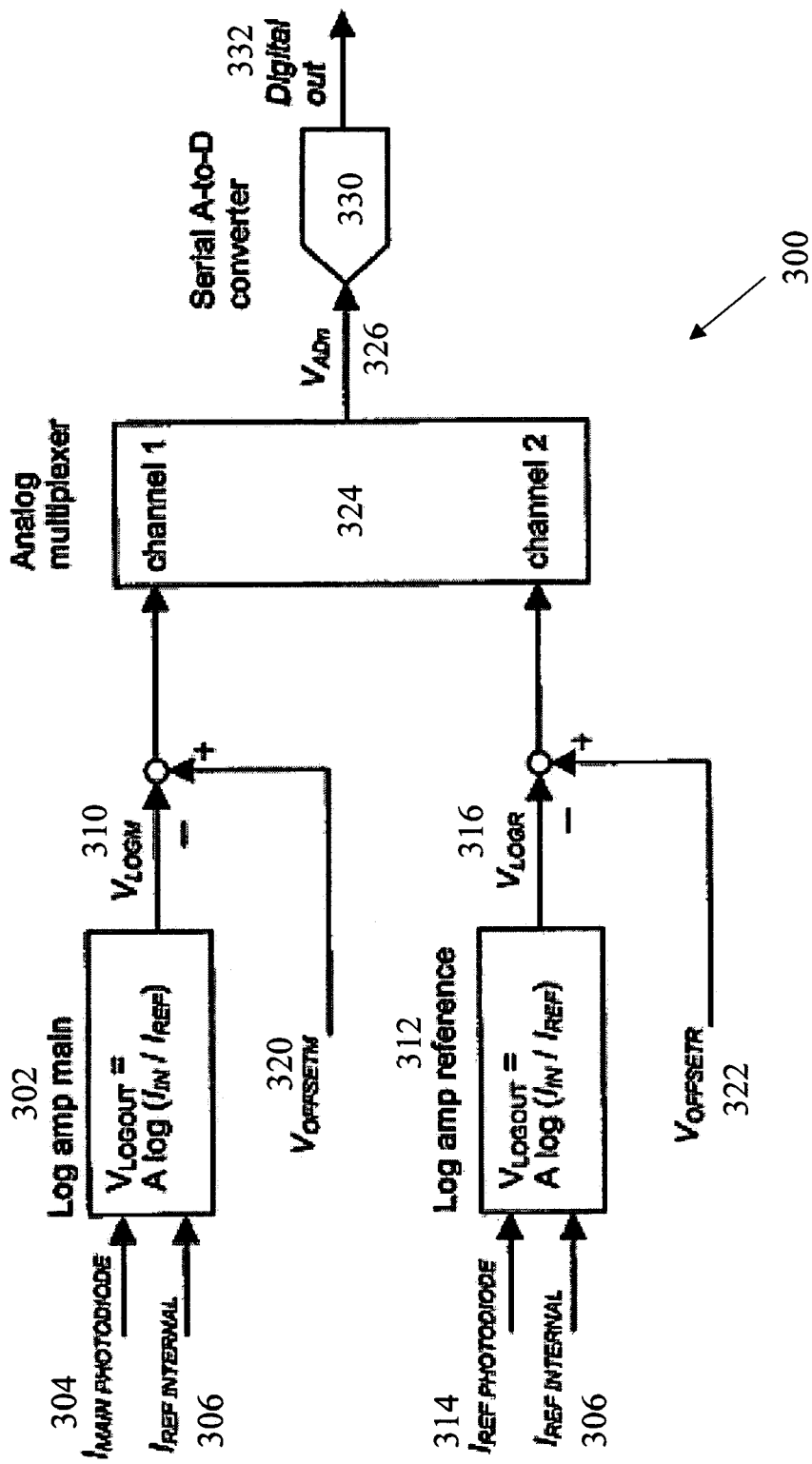
FIG. 7 is a schematic block diagram of one embodiment of front end circuitry for the cell density probe of FIG. 1.

In one embodiment, two log amps are employed. One log amp processes the output signal from the main measurement photodiode and one processes the output signal from the VCSEL reference photodiode. The reference channel may be used to compensate the main measurement reading to account for variation in source intensity with temperature. In another embodiment, the reference channel is used for diagnostics, and not in the A.U. measurement calculation. The reference channel readings may be compared to readings obtained over time and those recorded when the VCSEL was new, providing a measure of VCSEL degradation and operative health. The schematic block diagram in FIG. 7 shows the analog measurement front end 300 according to one embodiment of the present invention. As shown in FIG. 7, a main log amp 302 receives as inputs a main current $I_{main}$ 304 from the photodiode and an internal reference current $I_{ref\ internal}$ 306 and outputs a main signal voltage $V_{LOGM}$ 310 such that $V_{LOGM} = A \cdot \log(I_{main}/I_{ref\ internal})$. A reference log amp 312 receives as inputs a reference current $I_{ref\ photodiode}$ 314 from the photodiode and the internal reference current $I_{ref\ internal}$ 306 and outputs a reference signal voltage $V_{LOGR}$ 316 such that $V_{LOGR} = A \cdot \log(I_{ref\ photodiode}/I_{ref\ internal})$. Both the main signal voltage $V_{LOGM}$ and the reference signal voltage $V_{LOGR}$ may be adjusted using a main offset voltage $V_{OFFSETM}$ 320 and a reference offset voltage $V_{OFFSETR}$ 322, respectively. This offset adjustment allows a wide bipolar log amp output voltage to be maintained in a narrower A-to-D converter operation range while maintaining high resolution for the conversion process. The adjusted log amp outputs are routed through an analog multiplexer 324 to an A-to-D converter 330 to permit each channel to be converted into a digital measurement 332 separately. This digital output 332 is read by software using a microcontroller or microprocessor. In an embodiment offering greater precision than that detailed in the diagram, the offset voltages $V_{OFFSETM}$ 320 and $V_{OFFSETR}$ 322 may be routed through the analog multiplexer 324 as well, allowing each of them to be measured by the A-to-D converter 330 along with the adjusted log amp outputs. This permits software calculation of a very accurate log amp reading on each channel. In addition, if the offset voltages are controlled digitally using the same software, this provides a very flexible measurement circuit and a useful level of self-test capability.

Since absorbance is inherently a relative measurement, a zero reference reading to obtain a 100% light intensity measurement is obtained before a valid output can be generated. Once zero readings are obtained, they are stored and used to calculate future readings.

Fluorescence and Scattering Embodiments

Two additional methods that may employ probe configurations according to one or more embodiments of the present invention include fluorescence spectroscopy and scattering measurements.

Fluorescence is a phenomenon in which a molecule absorbs photons (light) at a given excitation wavelength and then re-emits photons at a different, longer wavelength (FIG. 1, top). The fluorescence excitation spectrum is the distribution of wavelength-dependent intensity that causes fluorescence while the fluorescence emission spectrum is the distribution of wavelength-dependent intensity of emitted energy.

Fluorescence has at least three advantages, including highly sensitive detection, high speed, and non-invasiveness. A fluorescence signal is proportional to the concentration of the substance being investigated. Whereas absorbance measurements can reliably determine concentrations only as low as several tenths of a micromolar, fluorescence techniques can accurately measure concentrations one million times smaller—pico- and even femtomolar. Additionally, very rapid changes in concentration may be monitored using fluorescence. Changes in fluorescence intensity on the order of picoseconds may be detected. Furthermore, the measurement process does not affect or destroy the sample or generate hazardous byproducts. Therefore, it may be used, for example, on living cells.

Figure 8:
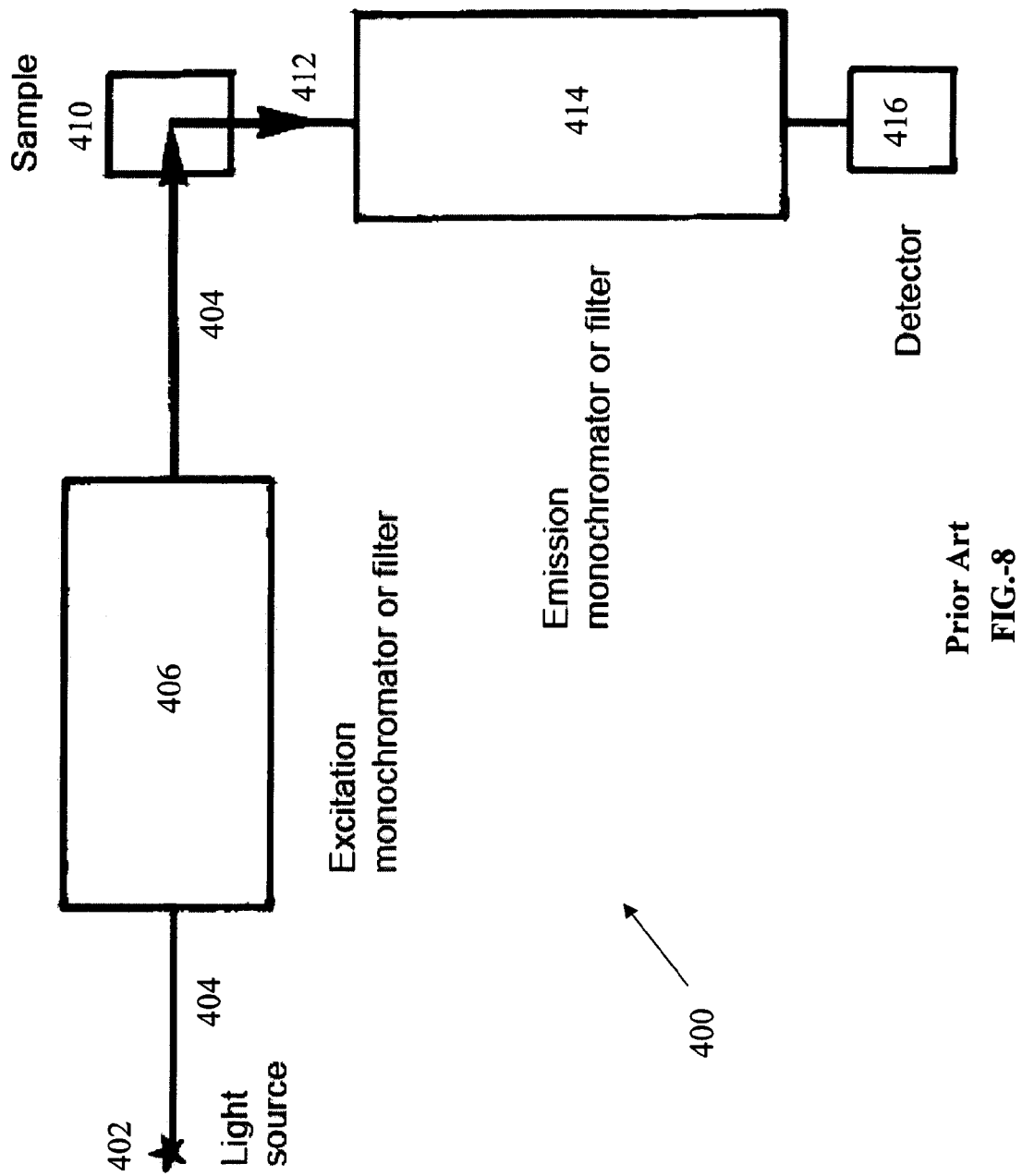
FIG. 8 is block diagram of a prior art spectrometer configuration for use in fluorescent or scattering measurements.

Fluorescence detection systems generally comprise an excitation source (which can have a monochromator or filter), a fluorescing material, wavelength filters or dispersive elements (monochormator) to isolate emission photons from excitation photons, and a detector that registers emission photons and produces a recordable output, usually as an electrical signal or a photographic image. Regardless of the application, compatibility of these four elements is advantageous for optimizing fluorescence detection. A typical spectrometer configuration 400 is shown in FIG. 8 in which a light source 402 passes a light beam 404 through an excitation monochromator or filter 406 and to the sample 410. The resulting emitted light 412 is directed to an emission monochromator or filter 414 and to a detector 416.

Although fluorescence spectroscopy is very similar to absorption spectroscopy, the effect of stray light can be much more severe in the case of fluorescence spectroscopy. Probe design must take this into account. Stray light is light derived from sources other than fluorescence that has the wrong wavelength. When this stray light enters the emission detection optical system, it may severely distort the fluorescence measurement. There are two types of stray light: scattered excitation light and Raman emitted light. A small amount of scattered light may be significant in comparison to the amount of emitted light, since the fluorescence effect is generally very weak. For a laser excitation source, however, the scattered light will be 100% polarized. Thus, setting a polarizer at 90° to the excitation polarization before the emission detector optical system will remove all or most of the scattered light. In addition to scattered stray light, Raman scattering may occur as the incident beam passes through a solvent, such as for example water. An incident photon may be absorbed by a water molecule and re-emitted with a lower or higher energy. The loss of energy is due to excitation of a vibrational level in the water molecule. The Raman scattering from $H_2O$ is typically approximately 3600 $cm^{-1}$ below that of the excitation light. Filters may be used to reduce the effects of scattered stray light by filtering the excitation light. Filters may also be used to reduce the effects of Raman scattering with alteration of the emission spectral shape.

If the sample absorbs light at the emission wavelength then the intensity and emission spectra may be changed by this absorption. In general, the spectra should be corrected for these inner filter effects. In some cases the absorption of the incident light is so high that the probe must be designed so as to use front face excitation. In this case, the emission collection optics are located inside a ring of excitation, to minimize the path length over which the emitted light must travel. FIG. 4a and FIG. 4b, which are discussed above, illustrate normal and front face probe geometries for a probe tip according to the present invention.

Fluorescence is a useful technique for studying molecular interactions in analytical chemistry, biochemistry, cell biology, physiology, nephrology, cardiology, photochemistry, and environmental science. As the theoretical underpinnings of fluorescence became more understood, a more powerfull set of applications emerged that yield detailed information about complex molecules and their reaction pathways. The binding of biochemical species can be easily studied in situ. Distances within macromolecules may be measured. The dynamics of the folding of proteins can be studied. Concentrations of ions can be measured inside living cells. Membrane structure and function may be studied with fluorescence probes. Drug interactions with cell receptors can be investigated. Minute traces of fluorescent materials can be detected and identified in mixtures. Oil samples can be finger-printed and identified by their fluorescence.

Fluorescence can provide useful information when monitoring fermentation processes by directly monitoring only the viable cells in the media. Specifically, a probe can be designed to exploit a common bioanalytical assay which is based on fluorescence from a metabolically active protein. The most common biomarkers are nicotinamide adenine dinucleotide (NADH), flavin adenine dinucleotide (FAD), tryptophan, typrosine, riboflavin, and pyridoxine. For example, live cells generate fluorescence from the reduced state of NADH while dead cells exhibit an absence of fluorescence from the oxidized state $NAD^+$. Endogenous fluorescence from these biomarkers can therefore be directly correlated to the viability of cells. The fluorescence signal is typically not affected by light scattering or reabsorption by the cell and growth medium.

Excitation light is generated at the excitation wavelength for a given biomarker, while detection must probe for fluorescence consistent at the appropriate emission wavelength. For NADH, FAD, and tryptophan, the probe optics would be designed as follows: NADH: 365 nm excitation and emission detection from approximately 375 nm to 720 nm, where emission peaks are observed at approximately 450 nm, FAD: approximately 460 nm excitation and emission detection from approximately 370 nm to 800 nm, where emission peaks are observed at approximately 520 nm, and Tryptophan: approximately 290 nm excitation and emission detection from approximately 300 to 570 nm, where emission peaks are observed at approximately 340 nm.

A nephelometer employs a light beam (source beam) and a light detector set to one side (usually 90 degreed) of the source beam. Particle (cell) density is then a function of the light reflected into the detector from the particles. To some extent, how much light reflects for a given density of particulates depends on the properties of the particles such as their shape, size, color, and reflectivity. Therefore, establishing a working correlation between turbidity suspended solids (a more useful, but typically more difficult quantification of particulates) must be established independently for each situation.

A more popular term for this instrument in water quality testing is a turbidimeter. In fermentation, it is called a turbidity monitor or probe. However, there can be differences between models of turbidimeters, depending upon the arrangement (geometry) of the source beam and the detector. A nephelometric turbidimeter always monitors light reflected off the particles and not attenuation due to cloudiness. The units of turbidity from a calibrated nephelometer are called Nephelometric Turbidity Units (NTU). A probe tip according to the present invention which could be used in conjunction with a nephelometer or other turbidty meter using a CSDL is shown in FIG. 4a. Note that its geometry is similar to that of the fluorescence probe, but that the detector filter 284 is set to the excitation, rather than the emission wavelength.

Additional example embodiments of techniques, such as shown in FIG. 4, to verify proper operation of the CDP are disclosed in copending U.S. patent application Ser. No. 10/856,885, filed 27 May 2004 and entitled "Method and Apparatus for Verifying Proper Operation of a Photometric Device, Such as a Cell Density Probe," which was invented under obligation of assignment to the same assignee as the present application, and which is incorporated herein by reference in its entirety.

For instance, the foregoing detailed description has set forth various embodiments of the devices and/or processes via the use of block diagrams, schematics, and examples. Insofar as such block diagrams, schematics and examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure. Such software or other machine-readable instruction can be stored at least one machine-readable medium and executable by one or more processors in order to provide the functionality described herein.

Specific examples have been provided herein for current and voltage values, binary values, signaling techniques, device types, features of such devices, protocols, settings, and so forth. It is appreciated that all such examples are merely for purposes of illustration and explanation, and are not intended to be limiting. The foregoing description of specific embodiments and examples of the invention have been presented for the purpose of illustration and description, and although the invention has been illustrated by certain of the preceding examples, it is not to be construed as being limited thereby. They are not intended to be exhaustive or to limit the invention to the precise forms disclosed, and obviously many modifications, embodiments, and variations are possible in light of the above teaching. It is intended that the scope of the invention encompass the generic area as herein disclosed, and by the claims appended hereto and their equivalents.

In addition, those skilled in the art will appreciate that the software mechanisms of taught herein for verifying proper operation of a photometric device and/or for performing other operations associated with the photometric device are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

All U.S. patents, U.S. patent application publications, U.S. patent applications, foreign patents, foreign patent applications and non-patent publications referred to in this specification and/or listed in the Application Data Sheet, are incorporated herein by reference, in their entirety.

What is claimed is:

1. An apparatus for measuring optical absorbance, comprising:
   i) a tip section comprising a first light source and a first detector, wherein the first light source emits a first light beam at a first wavelength across a first optical gap towards the first detector, such that the first detector receives the first light beam after the first light beam passes through the first optical gap and generates a first signal representative of the light received at the first detector;
   ii) an aperture positioned between the first light source and the first optical gap which aperture substantially prevent light from the first light source from reaching the first detector via a path through that portion of the tip section that is external to the first optical gap; and
   iii) a processor coupled to the first detector to determine an absorbance based on the first signal.

2. The apparatus of claim 1, wherein the first light source comprises a CSLD which is a VCSEL, a laser diode having a circularizing lens mounted on one of its facets, or a laser diode having a circularizing lens inside its package.

3. The apparatus of claim 1, wherein the first light source emits at a wavelength in the range of approximately 200 nm to 2000 nm.

4. The apparatus of claim 1 wherein the first light source emits at a near-infrared wavelength.

5. The apparatus of claim 1, further comprising a second detector to detect a characteristic of the first light beam prior to the first light beam being passed through the first optical gap.

6. The apparatus of claim 1, wherein the first and/or the second detectors comprise photodiodes.

7. The apparatus of claim 1, wherein that portion of the tip material that is external to the optical gap comprises polytetrafluoroethylene.

8. The apparatus of claim 1, wherein the tip section further comprises:
   a second light source and a second detector, wherein the second light source emits a second light beam at a second wavelength across a second optical gap towards the second detector, such that the second detector receives the second light beam after the second light beam passes through the second optical gap and generates a second signal representative of the light received at the second detector, such that the second signal is also coupled to the processor.

9. The apparatus of claim 1, further comprising a machine-readable medium coupled to the processor and having software stored thereon that can cooperate with the processor to determine the absorbance.

10. The apparatus of claim 1, further comprising electronic circuitry means for supporting operation of the apparatus.

11. The apparatus of claim 1, wherein the determined absorbance is related to cell density.

12. The apparatus of claim 1, further comprising either one or both a wired interface and a wireless interface coupled to the processor to allow communications with the apparatus.

13. The apparatus of claim 1, further comprising means for verifying proper operation of at least some elements of the apparatus.

14. The apparatus of claim 1, further comprising a second light source transmitting a second light beam parallel to the first beam and through the first optical gap onto a second photo-detector, the second light source emitting at a different wavelength than the first light source.

15. The apparatus of claim 14, wherein the first light source emits at a near-infrared wavelength and the second light source emits at an ultraviolet wavelength.

16. The apparatus of claim 14, wherein the first light source emits at a near-infrared wavelength and the second light source emits at a visible wavelength.

17. The apparatus of claim 14, wherein the first light source emits at a near-UV wavelength and the second light source emits at a visible wavelength.

18. An apparatus for making fluorescent measurements comprising:
   i) a tip section comprising a first light source and a first detector, wherein the first light source emits a first light beam at a first wavelength across a first optical gap which first beam is incident on a sample present in said first optical gap, such that the first detector receives fluorescent emissions occurring in the sample as a result of the incident light;
   ii) an aperture positioned between the first light source and the first optical gap which aperture substantially prevent light from the first light source from reaching the first detector via a path through that portion of the tip section that is external to the first optical gap; and
   iii) a processor coupled to the first detector to analyze the fluorescent emissions occurring in the sample as a result of the incident light.

19. An apparatus in accordance with claim 18 wherein said first detector is positioned off the axis of said incident first beam.

20. An apparatus in accordance with claim 18, wherein said light source is a CSLD and said apparatus further comprises:
   means for controlling the CSLD;
   means for initializing the photometric apparatus;
   means for controlling the photometric apparatus;
   means for communicating with the photometric apparatus; and
   a second light source and second detector.

21. An apparatus for making scattering measurements comprising:
   i) a tip section comprising a first light source and a first detector, wherein the first light source emits a first light beam at a first wavelength across a first optical gap which first beam is incident on a sample present in said first optical gap, such that the first detector receives light scattered by the sample as a result of the incident light;
   ii) an aperture positioned between the first light source and the first optical gap which aperture substantially prevent light from the first light source from reaching the first detector via a path through that portion of the tip section that is external to the first optical gap; and iii) a processor coupled to the first detector to analyze the light scattered by the sample as a result of the incident light.

22. An apparatus in accordance with claim 18, wherein said light source is a CSLD, and said apparatus further comprises:
   means for controlling the CSLD;
   means for initializing the photometric apparatus;
   means for controlling the photometric apparatus;
   means for communicating with the photometric device; and
   a second light source and second detector.

23. An apparatus in accordance with claim 22 wherein said first detector is positioned off the axis of said incident first beam.

* * * * *